(12) United States Patent
Gardiner

(10) Patent No.: US 11,833,263 B2
(45) Date of Patent: Dec. 5, 2023

(54) MOBILE DEVICE FOR OBJECT DISINFECTION AND/OR SANITIZATION

(71) Applicant: Kart Kleen LLC, Missoula, MT (US)

(72) Inventor: Jason Gardiner, Missoula, MT (US)

(73) Assignee: Kart Kleen, LLC, Missoula, MT (US)

( * ) Notice: Subject to any disclaimer, the term of this patent is extended or adjusted under 35 U.S.C. 154(b) by 0 days.

(21) Appl. No.: 18/110,591

(22) Filed: Feb. 16, 2023

(65) Prior Publication Data

US 2023/0256124 A1   Aug. 17, 2023

Related U.S. Application Data

(60) Provisional application No. 63/311,282, filed on Feb. 17, 2022.

(51) Int. Cl.
    *A61L 2/10*         (2006.01)

(52) U.S. Cl.
    CPC ............. *A61L 2/10* (2013.01); *A61L 2202/11* (2013.01); *A61L 2202/16* (2013.01); *A61L 2202/25* (2013.01)

(58) Field of Classification Search
    None
    See application file for complete search history.

(56) References Cited

U.S. PATENT DOCUMENTS

| | | | |
|---|---|---|---|
| 8,907,304 | B2 | 12/2014 | Kreitenberg |
| 9,144,618 | B2 | 9/2015 | Kreitenberg |
| 10,933,821 | B2 | 3/2021 | Line et al. |
| 2019/0022261 | A1* | 1/2019 | Dayton ..................... A61L 2/24 |
| 2020/0061223 | A1 | 2/2020 | Hallack |
| 2020/0306398 | A1 | 10/2020 | Ruiter et al. |
| 2021/0023251 | A1 | 1/2021 | Qiu et al. |
| 2021/0145184 | A1 | 5/2021 | Tigh, Jr. et al. |
| 2021/0260229 | A1 | 8/2021 | Satou |
| 2021/0369907 | A1 | 12/2021 | Umenei et al. |
| 2021/0393823 | A1 | 12/2021 | Childress et al. |
| 2021/0394590 | A1 | 12/2021 | Kyle et al. |
| 2021/0402936 | A1 | 12/2021 | Mann et al. |
| 2022/0001051 | A1 | 1/2022 | Subramanian et al. |

FOREIGN PATENT DOCUMENTS

KR    101241660 B1    3/2013

OTHER PUBLICATIONS

PCT Search Report and Written Opinion, dated May 17, 2023, for PCT Application No. PCT/US23/13241, 7 pages.

\* cited by examiner

*Primary Examiner* — Andrew Smyth
(74) *Attorney, Agent, or Firm* — Lee & Hayes P.C.

(57) ABSTRACT

A device may include a first arm and a second arm that are connected via one or more pivot points, one or more lamps that are disposed on the first arm and the second arm, and one or more support arms that enable the device to be positioned with respect to an object that is to be sanitized or disinfected. The one or more lamps emit light, such as UV light or UV-C light, that sanitizes or disinfects the object. The device may include a power source that provides electrical power to the one or more lamps and one or more handles that enable an operator of the device to transport the device and position the device with respect to the object. The device may also include an adjuster mechanism that enables the operator to adjust a distance between the device and the object.

20 Claims, 9 Drawing Sheets

US 11,833,263 B2

MOBILE DEVICE FOR OBJECT DISINFECTION AND/OR SANITIZATION

CROSS-REFERENCE TO RELATED APPLICATION

This application claims priority to, commonly-owned U.S. Provisional Patent Application No. 63/311,282 filed on Feb. 17, 2022, which is incorporated herein in its entirety by reference.

BACKGROUND

On a daily basis, people physically contact, without protection, potentially contaminated objects, and surfaces of such objects. Objects may include door handles, tables, rails, benches, shopping carts, seats within a vehicle, and the like. For instances, as a result of people riding in, or touching, seats or other surfaces of a vehicle, these surfaces are exposed to various types of pathogens, including viruses, bacteria, and so on. When the next person rides in the vehicle, the pathogens may be unintentionally passed to that person, possibly resulting in sickness or death. The likelihood of illness is significantly high considering the type and number of vehicles that include seats touched by different people on a daily basis, including cars (e.g., personal cars, rideshare cars, police cars, ambulances, fire trucks/engines, taxi cabs, shuttles, etc.), busses, trains, airplanes, commuter vans, shuttles, and so on. Accordingly, there is a need to sanitize and disinfect surfaces of a vehicle, and the surfaces of vehicle seats in particular.

BRIEF DESCRIPTION OF THE DRAWINGS

The detailed description is set forth with reference to the accompanying figures. In the figures, the left-most digit(s) of a reference number identify the figure in which the reference number first appears. The use of the same reference numbers in different figures indicates similar or identical items or features.

DETAILED DESCRIPTION

Figure 1:
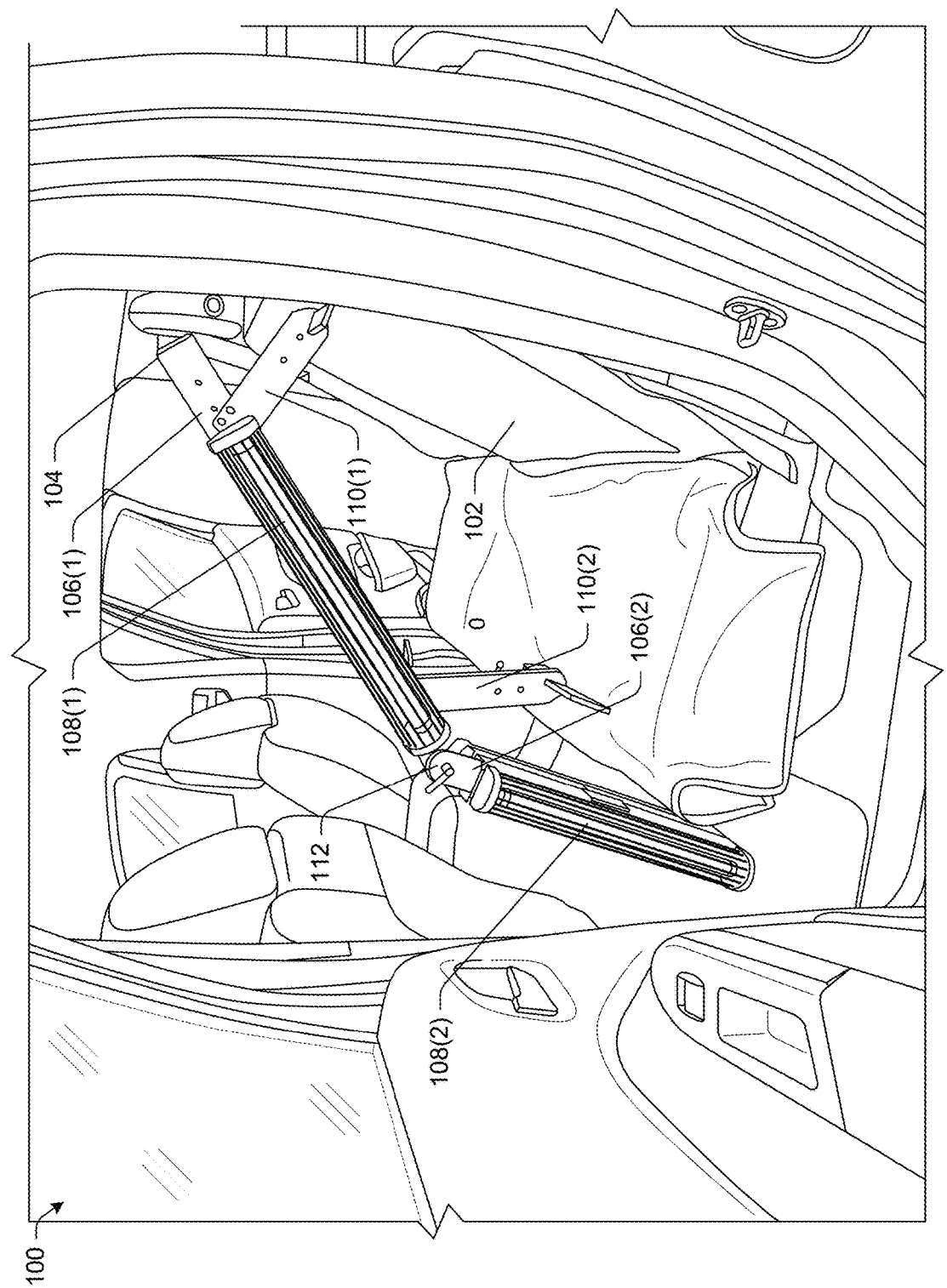
FIG. 1 is a pictorial diagram of an illustrative device that includes one or more lamps that are configured to sanitize and/or disinfect surfaces of an object, such as seats of a vehicle.

In the context of public health and safety, people in public and private spaces encounter microorganisms on a daily basis. Some of these microorganisms, such as bacteria and/or viruses, may be harmful to people. A pathogen (i.e., a germ, bacteria, a virus, etc.) may be any type of microorganism that may cause or produce a disease or illness. *E. coli* (i.e., a pathogenic bacteria) may cause at least food poisoning that is harmful to humans. In addition, instances of *E. coli* with respect to food products frequently cause recalls of those food products due to potential food contamination. A recall, such as a request from a store, a manufacturer, or a producer to return a contaminated product, may cause costly disruptions in the business. In particular, a physical environment (e.g., a retail store, a grocery store, a medical facility, a vehicle, etc.) may have a steady flow of people physically interacting with objects and surfaces (e.g., door handles, shopping carts, vehicle handles, vehicle seats, etc.) during their hours of operation and, therefore, may be susceptible to harboring harmful pathogens. For instance, food preparation businesses including restaurants and delis may be vulnerable to harboring *E. coli* due to the nature of their business handling raw and uncooked food. Moreover, surfaces in certain vehicles (e.g., police vehicles, first responder vehicles, taxis, rideshare vehicles, shuttles, busses, trains, airplanes, etc.) may be touched by multiple people on a daily basis. Therefore, to protect the health of safety of customers/individuals, it may be necessary to ensure the sanitization of objects that may be in physical contact with consumers, customers, employees, etc. In addition, limiting the exposure of potentially harmful pathogens may benefit businesses by avoiding the consequences of harboring potentially harmful pathogens (e.g., avoiding recalls, avoiding store/vehicle closures, avoiding lawsuits, etc.).

With respect to the sanitization of physical objects, there is a need for techniques, including processes and apparatuses, that facilitate efficient, high-quality, and reliable sanitization and or disinfection of physical objects and surfaces. In particular, physical objects and surfaces, which may be interchangeably referred to as "objects," "items," or "surfaces" herein, may be located within a physical environment (e.g., a vehicle, a chair/seat, etc.). These objects (e.g., vehicle surfaces, vehicle seats, chairs/seats, hospital beds, wheelchairs, etc.) may be accessible for physical contact by customers and/or employees. Because these objects are physically handled by customers and/or employees during the course of business, and since these objects may be in physical contact with various individuals on a daily basis, there is a need to sanitize the objects regularly to guard against potentially harmful pathogens that attach to the objects/surfaces. For instance, a multiple individuals may ride in a vehicle, and sit in a particular seat within the vehicle, multiple times per hour, per day, and per week. If the vehicle, or a surface of the vehicle (e.g., a door handle, a seat, a seatbelt, etc.) were to be harboring a harmful pathogen, each of the multiple customers that rode in the vehicle may have been unknowingly exposed to the harmful pathogen.

Traditional techniques to clean the inside of a vehicle may include using traditional cleaners/cleaning agents and cleaning tools, such as towels, rags, and/or brushes. However, these techniques often neglect eliminating sanitation threats at a microbial level. Such techniques may not sanitize/disinfect each surface of the object, are time consuming, and use a significant amount of resources/supplies (e.g., cleaning solution, rags, paper towels, etc.). Further, these techniques may result in wear and tear of an object/surface because they require physically touching the object/surface with a cleaning agent and/or a cleaning tool. For instance, as a result of constantly cleaning vehicle seats in response to multiple individuals riding in the vehicle, the seats may become worn, may discolor, may lose their shine, may tear or rip, and so on.

As a result, there is a need for efficient, high-quality, and reliable results sanitizing and/or disinfecting surfaces of objects, including surfaces within a vehicle, such as seats, door handles, seatbelts, and other surfaces within the vehicle. The systems and processes described herein utilize ultraviolet (UV) light, UV-C light, and/or any other type of light that is capable of killing/eliminating pathogens to sanitize/disinfect an object. In particular, the device described herein may include two pivotable and/or rotatable arms that each include one or more lamps that emit light towards an object to be sanitized/disinfected. Each of the arms may pivot and/or rotate around a pivot (or pivot point) that is disposed between the two pivotable arms. As a result, the lamps are able to emit light in different directions depending on the object/surface desired to be sanitized/disinfected. The device may include one or more support arms or structural supports that allow the device to be positioned over, underneath, or to the side of the object/surface to be sanitized/disinfected. The device may also include one or more handles that allow the device to be placed in the proper position prior to the lamp(s) emitting light toward the object/surface. For instance, the handle(s) of the device may be used to place the device on a seat of a vehicle that is to be disinfected/sanitized, to remove the device, and/or to transport the device when not in use. The device may include a power source and/or power cord to supply power to the lamp(s). Once the lamp(s) have emitted light towards the object/surface to be sanitized/disinfected for a period of time, and as stated above, the device may be removed using the handle(s), such that an individual avoids the risk of being burned by the lamp(s).

In some embodiments, the device may have two arms that each permanently or removably attach to the object, such as different sides of a seat/seats to be sanitized or disinfected. A first end of the arms may be coupled to the object and a lamp assembly may be coupled/attached to second ends of the arms such that the lamp assembly is disposed between the arms. The lamp assembly may include one or more lamps that are configured to emit light toward the object. The arms and the lamp assembly may be an upper mounted unit in which the device rotates downwards or a lower mounted assembly in which the device rotates upwards. Regardless of the direction of rotation of the device, the device may cease moving at different positions such that the lamp(s) may emit light towards different surfaces of the object (e.g., the seat(s)). The device may emit light directed towards the object at any number of positions/locations. The lamp(s) may refrain from emitting light when the device is positioned at the lower position and/or the upper position. That is, the upper position or the lower position may be a start position or an end position of the device. As a result, the device may emit light directed towards the object at multiple different positions such that different surfaces of the object are sanitized/disinfected by the light.

Therefore, the systems and techniques described herein address the above challenges with respect to cleaning and sanitizing objects/surfaces. The device described herein facilitates a primarily touchless process to sanitize/disinfect an object/surface in order to reduce wear and tear and/or damage to the object/surface that could potentially occur as a result of not using the device and techniques described herein.

FIG. 1 is a pictorial diagram of an illustrative device that is configured to sanitize or disinfect an object and/or surface of an object (collectively referred to herein as "object"). The object 102 may be sanitized/disinfected by the device 104, which may include one or more arms 106 (shown as 106(1) and 106(2)) and one or more lamps 108 (shown as 108(1) and 108(2)). The arms 106 may be supported by, and positioned over the object 102 using, one or more support arms 110 (shown as 110(1) and 110(2)). The arms 106 may be connected to one another via a pivot 112 (or pivot point), which may allow the arms 106 to rotate, pivot, bend, turn, etc. via/around the pivot 112.

The system and processes described herein are directed to a device 104 for sanitizing and disinfecting surfaces of objects 102, such as seats of a vehicle, using light emitted onto the surfaces of the objects 102. As described herein in additional detail, the light may include UV light, UV-C light, and any other type of light that is capable of killing/eliminating pathogens (collectively referred to as "light") that is emitted by UV lamps 108, UV-C lamps 108, and any other lamps/lights that emit the light (collectively referred to as "lamps 108"). In particular, the device 104 may include one or more pivotable and/or rotatable arms 106 that may or may not be removably attached to a portion of the vehicle, such handles, seats, or other physical structures of the vehicle. The pivotable arm(s) 106 may include one or more lamps 108 that are detachably attached to the pivotable arm(s) and that emit light in a direction toward the surface(s) of the object 102 (e.g., a seat). The pivotable arm(s) 106 may remain in a fixed position or may rotate upwards and/or downwards to cause the lamps to emit light towards the upper portion of the object 102 (e.g., the upper portion of the seat) and the lower portion of the object 102 (the lower portion of the seat), respectively. The pivotable arm(s) 106 may be rotated to different positions in which the lamps may emit light towards the object 102 in different positions. The rotatable arm(s) 106 may also rotate or move based on a configuration of the object 102/seat. The lamps 108 may be moveable or rotatable such that the lamps 108 can be directed towards different portions of the object 102/seat, and such that the lamps 108 can emit light towards other surfaces of the object 102 and/or surfaces of different objects 102 (e.g., interior of car doors, the floor, seat belts, the ceiling, dashboard, steering wheel, etc.). The rotatable arms 106 and corresponding lamps 108 may be used to sanitize/disinfect front seats or back seats of a vehicle (including single seats, double seats, triple seats, etc.), as well as any seat in a vehicle that has more than two rows of seats (e.g., airplanes, busses, trains, etc.). In addition, the rotatable arm(s) 106 may be adjustable or extendable for proper placement and/or position of the lamps 108 over the object 102/seat.

In certain embodiments, the device 104 may be placed onto, to the side of, or over, one or more surfaces of an object 102, such as seats, using built in handles. As described herein, the one or more handles may be proximate to the lamps 108. Although the lamps 108 may be of any number and may be disposed in any configuration/position, a total of four lamps 108 may be included on the device 104 and disposed on the arm(s) 106. A first handle may be disposed proximate to two upper lamps 108 (e.g., 108(1)) that are disposed on an upper arm 106(1) ("upper lamp assembly") and a second handle may be disposed proximate to two lower lamps 108 (e.g., 108(2)) that are disposed on a lower arm 106(2) ("lower lamp assembly"). The one or more arms 106(1) and 106(2) may allow the device 104 to be positioned suitably based on the size, shape, and orientation of the object 102. As a result, the upper lamp assembly and the lower lamp assembly may apply light onto the same portions of the object 102, or onto different portions of the object 102.

The device 104 may also have one or more support arms 110 (e.g., 110(1) and 110(2)) that contact the object 102 to be sanitized/disinfected and that support the device 104 when the device 104 is in use. As shown, although any number of support arms 110 (or legs) may be present, the device 104 may have two support arms 110, which maintain contact with the surfaces of the object 102 and allow the device 104 to be held in place while the lamp(s) 108 apply light towards the object 102. The support arms 110 may be of any shape, size, width, length, and thickness, may be made of any material, and may be disposed at any location of the device 104 such that the device 104 is able to remain stationary with respect to the object 102 while the lamps 108 of the device 104 are emitting light that is sanitizing/disinfecting the object 102. The support arms 110 may also be adjusted in any direction or angle (e.g., upwards, downwards, sideways, etc.) in order for the device 104 to be positioned over, underneath, to the side of, etc. the object 102 and in order for the device 104 to be in a suitable position to apply light to the object 102. For instance, the support arms 110 may be adjusted in order to adjust the upper lamp assembly and/or the lower lamp assembly based on the size, shape, configuration, etc., of the object 102. That is, the support arms 110 may be adjusted such that light emitted from the lamps 108 may be directed towards the seats depending on the current configuration of the seats (e.g., upright, reclined, etc.).

Once the rotatable arm(s) 106 and the corresponding lamps 108 are in a suitable position/place to emit light towards the object 102, the lamps 108 may be powered on in various different manners. As described and illustrated elsewhere, and in the context of a vehicle, the lamps 110 may be powered on via a power cord that is routed outside of the vehicle via a vehicle door, a vehicle window, a vehicle sunroof, and so on. Regardless of the object 102 to be sanitized/disinfected, the power cord may be plugged into any available power source, such as a wall outlet, possibly via an extension cord. In other embodiments, the lamps 108 may be powered via one or more batteries (rechargeable or not) that are separate from a battery of the vehicle. Moreover, the lamps 108 may be powered by a power source within the vehicle, such as a power outlet, a USB adapter, a cigarette adapter, etc., which may be powered by the battery of the vehicle. An inverter may also be used as a power source for the lamp(s) 108. Thus, the system may be powered by the battery of the vehicle itself.

Once the lamps 108 are connected to a power source, the lamps 108 may emit light towards the object 102 (or seats or other surfaces) for a suitable amount of time to disinfect/sanitize the object 102. The device 104 may have some type of input mechanism (e.g., a switch, button, lever, etc.) that a user may actuate in order to turn on/off the lamps 108. The amount of time in which the light is applied to the seat/surface may vary (e.g., 10 seconds, 30 seconds, 1 minute, 2 minutes, etc.). As stated above, the lamps 108 may be powered on/off by a user or the lamps 108 may be powered on for a predetermined amount of time. As described in additional detail, the user may specify the predetermined amount of time via an input mechanism associated with the device 104. In other embodiments, the lamps 108 may be powered on/off and the time in which the light is applied may be controlled via a remote control or a mobile application residing on a device (e.g., a mobile telephone, a tablet device, a desktop/laptop computer, etc.) different than the device 104. Moreover, the device 104 may be associated with one or more sensors that may detect when a door of the vehicle has been opened. Upon the sensor(s) receiving such sensor data, which indicates that a door has been opened, the lamps 108 may be powered off. Moreover, the sensors may also detect an orientation of the device 104 such that the lamps 108 may be powered off if the orientation of the device 104 changes more than a threshold amount. This may occur if the device 104 shifts or slips as the lamps 108 are applying light to the object 102 (e.g., a seat).

Figure 4:
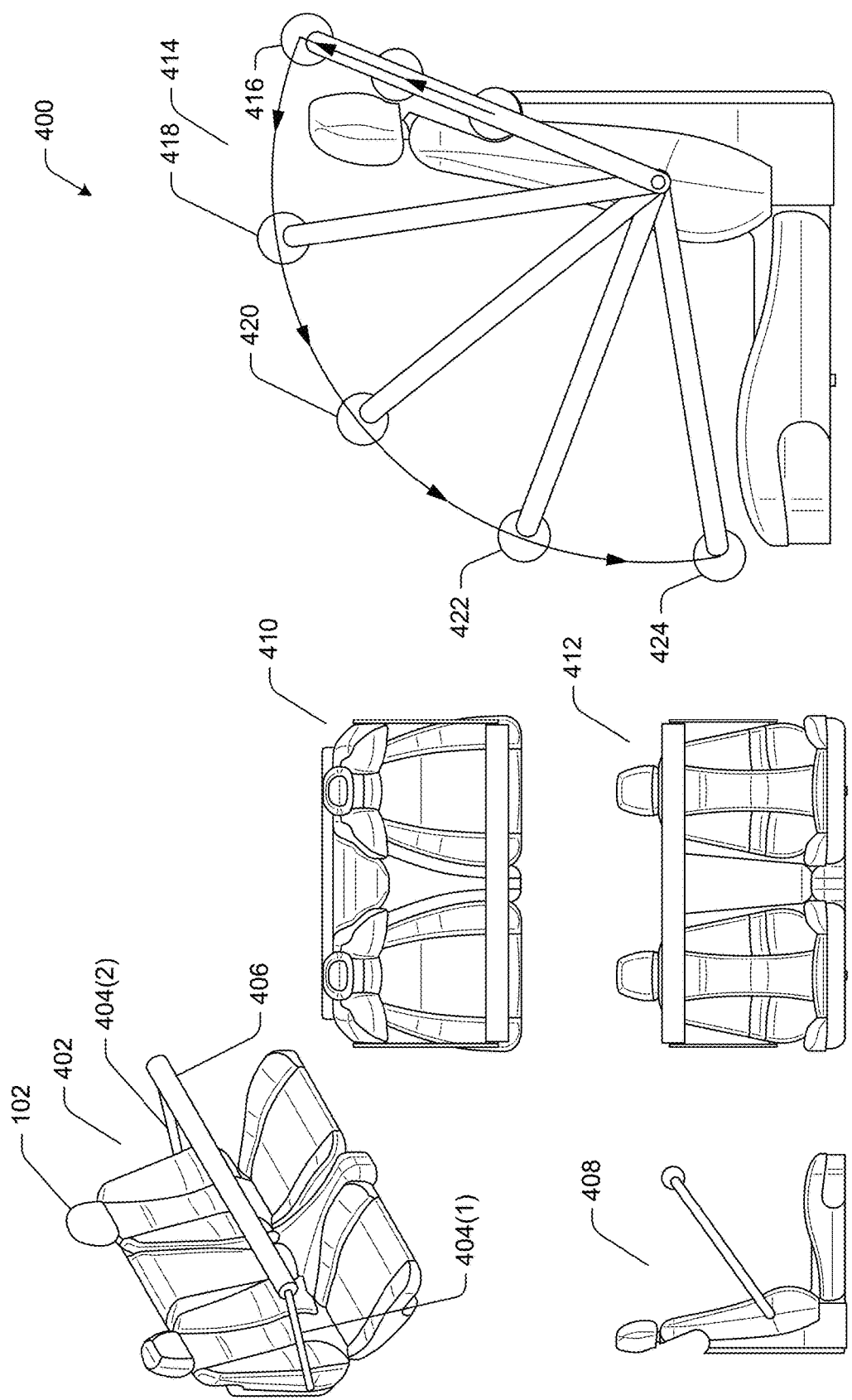
FIG. 4 is a pictorial diagram of an illustrative device that is integrated into a chair or seat in an upper mounted configuration.
Figure 5:
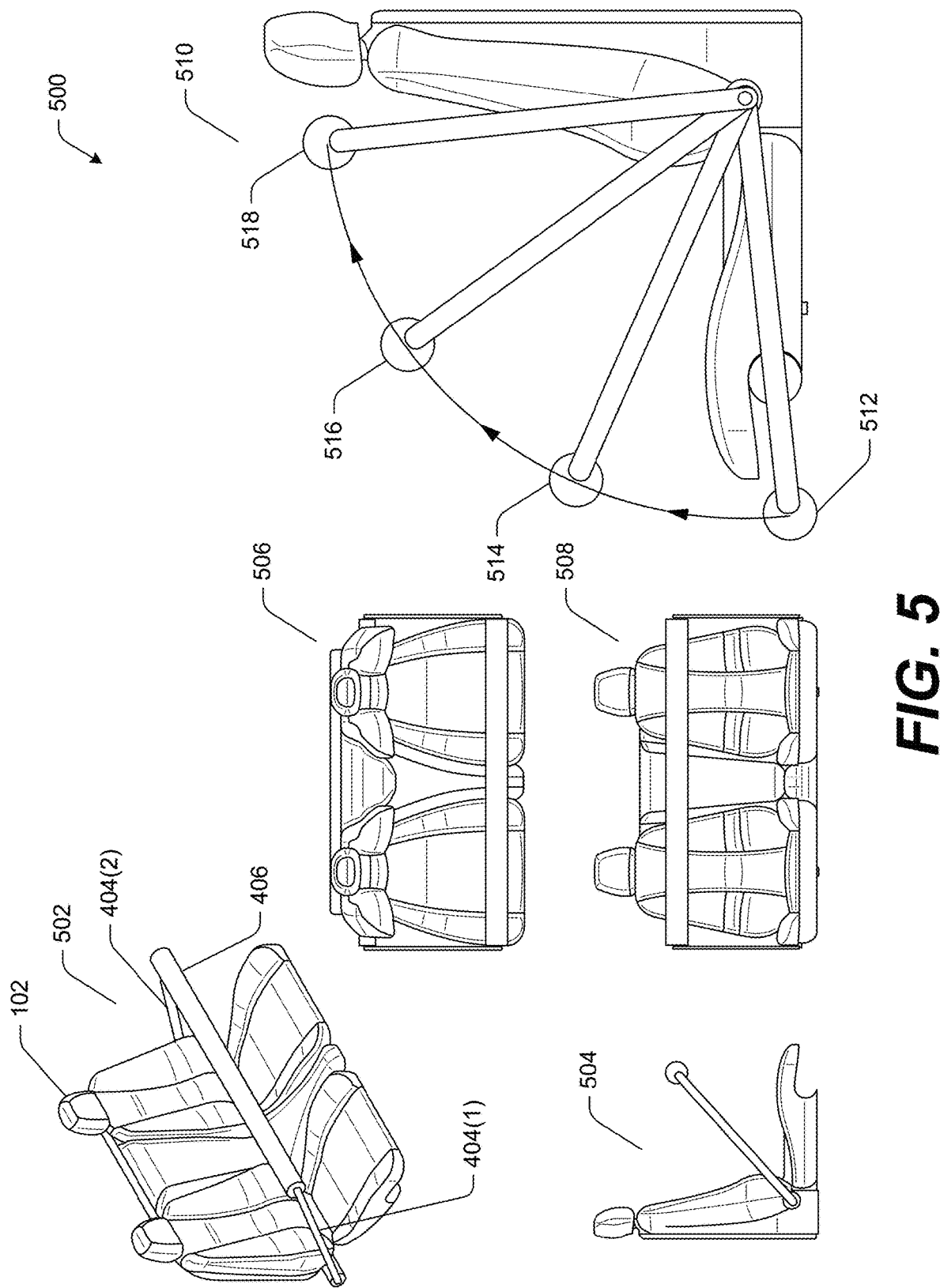
FIG. 5 is a pictorial diagram of an illustrative device that is integrated into a chair or seat of in a lower mounted configuration.

As described herein, any number of lamps 108 may be utilized and the arms 106 may be made of any suitable material, such as metal (e.g., aluminum, steel, etc.), plastic, wood, etc. The arms 106 may be connected to one another via a pivot 112, such as an adjustable pivot point, that allows the arms 106 to rotate and/or bend. The support arms 110 of the device 104 may be adjustable such that the lamps 108 can be positioned at different heights/distances from the surface of the object 102 to be sanitized/disinfected (e.g., the seats of the vehicle). The device 104 may include an upper mounted unit configured to emit light towards the upper surfaces/portions of the seat, a lower mounted unit configured to emit light towards the lower surfaces/portions of the seat, or both. For instance, the upper mounted unit may include the arm 106(1), the lamp(s) 108(1), and the support arm(s) 110(1), and the lower mounted unit may include the arm 106(2), the lamp(s) 108(2), and the support arm(s) 110(2). However, as illustrated in FIGS. 4 and 5, the device 104 may be attached to a middle portion or different sides of the seat and thereby be rotated such that the lamps 108 apply light to both the upper surfaces/portions and the lower surfaces/portions of the seat.

In the context of a vehicle, one or more safety curtains may be placed over the side windows, front windshield, rear windows, sunroof, etc. of the vehicle prior to the lamps 108 being powered on within the vehicle, thereby preventing possible eye injury resulting from the UV/UV-C light escaping through glass surfaces of the exterior of the vehicle. The device 104 may utilize UV-C germicidal irradiation (UVGI), which interacts with the DNA and RNA polymeric molecules that comprise the genomes of microorganisms. Although this disclosure describes exposing seats of a vehicle to UV/UV-C light to sanitize/disinfect the seats, the lamps and the corresponding UV/UV-C light may be used to sanitize/disinfect any type of surface. Moreover, in certain embodiments, a disinfectant spray may be applied to the seats in addition to, or instead of, the light emitted by the lamp(s) 108. The disinfectant spray may be sprayed onto the object 102 by the device 104 (e.g., nozzles of the device 104) or the disinfectant spray maybe sprayed onto the object 102 in a different manner (e.g., a spray bottle). Provided that a disinfectant spray is utilized, one or more fans may dry the surface, possibly using purified air. The fans may be part of the device 104, may be coupled to the device 104 in some manner, or may be separate from the device 104.

As illustrated in FIG. 1, although the device 104 may be utilized to sanitize or disinfect any object 102, the device 104 may be situated within the interior of a vehicle in order to sanitize/disinfect seats (or other surfaces, such as door handles, doors, headrests, etc.) of the vehicle. The vehicle shown is a car or truck, but the device 104 can be used in the context of other vehicles (e.g., busses, trains, airplanes, etc.) and/or other objects 102 (e.g., dining chairs, desk chairs, couches, desks, tables, etc.). As shown, the device 104 is situated with respect to the backseat of the vehicle, and the arms 106 of the device 104 may each have one or more lamps 108 that emit light towards different surfaces of the seats of the vehicle. Here, the upper arm 106(1) is situated such that the lamp 108(1) can emit light towards the top portion of the seat, the bottom portion of the seat, or both. The upper support arm 110(1) may be coupled or connected to the upper arm 106(1) and may support the device 104 by being placed on the top or upper portion of the seat. Moreover, the lower arm 106(2) is situated such that the lamp 108(2) can emit light towards the top portion of the seat, the bottom portion of the seat, or both. The lower support arm 110(2) may be coupled or connected to the upper arm 106(1) or the lower arm 106(2) and may support the device 104 by being placed on a lower portion of the seat. The upper support arm 110(1) and the lower support arm 110(2) may allow the device 104 to be positioned above the seat such that the lamps 108 of the device 104 may emit light directed to all surfaces of the seat.

The pivot 112 (or pivot point) may allow the arms 106 of the device 104 to bend to different configurations, and desired configuration of the arms 106 may be based on the orientation/configuration of the seats, the type of vehicle, which seats are being sanitized/disinfected, and so on. The pivot 112 may also allow the arms 106 of the device 104 to be rotatable such that the lamps 108 of the device 108 may emit light in different directions. For instance, the pivot 112 may allow the arms 106 to be rotated to the left or the right such that different portions of the seat or different surfaces of the vehicle can be sanitized/disinfected. That is, while the device 104 is positioned in the same place within the vehicle, just the arms 106 may be rotated to cause the lamps 108 to emit lights towards a different portion of the same seat, a different seat, or a different surface of the vehicle, such as the doors, the windows, the ceiling, and so on. In some embodiments, the lamps 108 may emit light in multiple different directions at the same time and/or the lamps 108 may be rotatable while the arms 106 of the device 104 may remain stationary or fixed.

Once the device 104 is in a suitable position, the lamps 108 may be powered on and the lamps 108 may emit light onto the object(s) 102 (here, the seats) for a period of time, which may be predetermined, manually set, or adjustable. The lamps 108 may also have some type of protective surface or a lamp assembly, such as a housing, a shield, or a cage, that prevents an object making contact with the lamps 108 while the lamps 108 are on (or are still hot after use). Such protective surface may prevent burns by a user, damage to an object that comes in contact with the lamps 108, and potential fire hazard/risks. Once the object 102 has been exposed by the light emitted by the lamps 108 for a desired period of time, the lamps 108 may be allowed to cool and may be removed from the vehicle, possibly using one or more handles of the device 104. The device 104 may also be moved to a different position in order to sanitize/disinfect other surfaces of the vehicle. Further, in a non-vehicle embodiment, the device 104 may be moved to sanitize/disinfect a different surface of the object 102 or a different object 102.

In some embodiments, the object(s) 102 to be sanitized/disinfected by the device 104 may be of any size, shape, material, etc. and the device 104 may also be of any size, shape, material, orientation, configuration, etc. That is, the device 104 may be of any height, length, and/or width. The device 104, and different components of the device 104, may also be made of any material or any combination of materials, such as any type of metal, any type of plastic, any type of wood, any synthetic or semi-synthetic polymer material, or any other suitable rigid, semi-rigid, or non-rigid material. For instance, and as described herein, the device 104 may sanitize/disinfect smaller objects 102, or the surfaces of such objects 102, such as shopping carts, hospital beds, wheelchairs, food preparation carts/tables, vehicle seats, vehicle door handles, other surfaces within vehicles, chairs, tables, furniture, beds, etc. Other objects 102 that may be sanitized/disinfected by the device 104 may include clothing (e.g., inmate clothing, uniforms, scrubs or other medical clothing, etc.), gear (e.g., tactical gear, riot gear, police gear, firefighting gear, helmets, etc.), PPE (e.g., face masks, face shields, gloves, headwear, goggles, etc.), and so on. However, the device 104 may be of a suitable size to sanitize/disinfect larger objects 102. For the purposes of this discussion, the device 104 may be built to any size and/or may be adjustable to any size, thereby allowing the device 104 to clean, disinfect, and/or sanitize objects 102 (and the surfaces thereof) of any size.

As described herein, the device 104 may have any number of lamps 108, and the device 104 depicted in FIG. 1 includes four lamps 108—two lamps 108 located proximate to the upper arm 106(1) and two lamps 108 located proximate to the lower arm 106(2). The lamps 108 may be disposed on opposite sides of each arm 106. The lamp(s) 108 may be configured to emit light at a wavelength outside of the visible spectrum that disables, breaks down, and/or destroys pathogenic organisms (e.g., bacteria, viruses, etc.), DNA, RNA. For instance, the lamps 108 may be germicidal UV lamps. The lamp(s) may be housed in lamp housings to provide directional application of the light to the object(s) 102, and the lamp housings may prevent harm/damage to users of the device 104, the object 102, or different objects. The lamp housings may provide a direction for the lamps 108 to emit light, thereby assisting in the application of light to the object(s) 102. The lamp housings may also prevent at least a portion of the light emitted from the lamps 108 from being emitted in a direction away from the object(s) 102.

As described elsewhere, the lamps 108 referenced throughout this disclosure may emit UV light, UV-C light, etc. that is sufficient to eliminate or destroy pathogens, bacteria, viruses, and so on. The size of the lamps 108 may vary such that the frequency and intensity of light output can be adjusted. That is, the size, type, and position of the lamps 108 may vary to emit light of a sufficient intensity at varying wavelengths. An example wavelength may be 254 nanometers, which is highly damaging to nucleic acids and other pathogens, viruses, bacteria, etc., when they are exposed to light having that particular wavelength. However, other wavelengths of light may also be utilized to disinfect and/or sanitize objects 102 that are exposed to the light. The duration or amount of light emitted towards an object 102 to sanitize/disinfect the object 102 may be dependent upon the variance of the lamps 108 (e.g., size, type, distance between lamp 108 and object 102, etc.).

In some embodiments, the lamps 108 may be detachably affixed/coupled to the arms 106 of the device 104 such that the lamps 108 may be moved to different locations, shifted, rotated, moved to a different angle, etc. For instance, a lamp 108 associated with an arm 106 of the device 104 may be moveable and/or rotatable such that the lamp 108 may still be coupled to the arm 106, but the lamp 108 may be able to emit light in different directions. In order to make the lamps 108 moveable and/or rotatable, the lamps 108 may be affixed to the arm 106/device 104 via rails, brackets, or any other coupling mechanism that allows the lamps 106 to move or allows the direction of the emitted light to be adjusted. This may allow the lamps 108 to be focused on the object 102 to be sanitized/disinfected based on the size, type, shape, etc. of the object 102. A frequency or wavelength of light emitted by the lamps 108 may also be adjusted (e.g., increased, decreased, etc.) prior to, or during, sanitization/disinfection of the object 102. The lamps 108 may be removed from the device 104, or additional lamps 108 may be added to the device 104. The bulbs of the lamps 108 may also be removed/replaced in the event of damage, breakage, malfunction, etc.

The device 104 may be transitioned between an expanded/uncollapsed state or an expanded/uncollapsed configuration (collectively referred to herein as "expanded configuration") and an unexpanded/collapsed state or an unexpanded/collapsed configuration (collectively referred to herein as "collapsed configuration"). When in use and when an object 102 is underneath the device 104 and is ready to be sanitized or disinfected, the device 104 is in the expanded configuration. From the expanded configuration, device 104 may be transitioned to the collapsed configuration, which may provide for easier or more efficient transport and storage. As illustrated in FIG. 1, the device 104 is in the expanded configuration since the device 104 is in a configuration to emit light towards the object 102 (e.g., a surface of the seat). The device 104 may be rotated, pivoted, or bend with respect to the pivot 112 in order to transition the device 104 between the expanded configuration at which the device 104 may be utilized and the collapsed configuration in which the device 104 is stowed for moving, repositioning, or transport.

Instead of, or in addition to, the device 104 including the support arms 110, the device 104 may be suspended over the object 102 and/or may be attached to some other structural component that does not come in contact with the object 102. For instance, the device 104 may be supported by a platform, stand, pole, etc. such that the device 104 is suspended over, underneath, or to the side of the object 102 to be sanitized/disinfected.

In some embodiments, the device 104 may include one or more sensors that detect the object 102, or one or more surfaces of the object 102. The sensor(s) may include an active or passive infrared sensor, a microwave sensor, an area reflective sensor, an ultrasonic sensor, a photo optic motion sensor, or any other type of sensor that is configured to collect sensor data that indicates that an object 102 (or a surface thereof) has been detected within a threshold distance from the device 104. The device 104 may include any number of sensors and the sensor(s) may be positioned/configured on any portion of the device 104, such as the arms 106, the lamps 108, the support arms 110, the pivot 112, and so on. In some instances, the object(s) 102 may be configured to contain a radio transmitter that may send a coded and/or encoded signal (e.g., radio wave) that is received by a receiver on the sensor(s). The radio transmitter may also be placed on the object 102, or near the object 102. The sensor(s) may detect the object(s) 102 based on receiving a signal emitted from the object(s) 102. In response to the sensor(s) detecting the object(s) 110, the device 104 may send a signal (e.g., audio, text, visual indicators) indicating that the device 104 is in a position to initiate disinfection and/or sanitization of the object(s) 102. In other embodiments, once the sensor(s) detect the object 102, or once the object 102 is determined to be at or within a threshold distance from the sensor(s) (e.g., 6 inches 12, inches, etc.), the device 104 may be powered on and the lamp(s) 108 of the device 104 may begin emitting light directed towards the object(s) 102.

The UV curtains described above may be positioned such that the light emitted by the lamps 108 is directed only at the object 102 and not elsewhere, such as in a direction associated with a user or other objects. The UV curtain may also be coupled to, or otherwise associated with the device 104. For instance, the UV curtain may be placed around the device 104 and the object 102 to be sanitized/disinfected in order to limit the amount of light that is not emitted directly towards the object 102. The UV curtain may be a material, such as amber-tinted poly vinyl chloride or other suitable materials, to block at least a portion of the light emitted from the lamps 108. In some instances, the UV curtains may be fastened or secured to the ground, a surface different than the object 102, and/or the device 104 itself via one or more fasteners. The fasteners may be based on a material in which the UV curtain is attached. The fasteners may include screws, anchors, nails, spikes, concrete/cement, adhesive, or other suitable fasteners to permanently or removably fix the UV curtain to the ground, surface, object 102, etc. The UV curtain may be configured to block an entirety or a portion of the light emitted by the lamps 108 by surrounding or encapsulating the device 104, or at least the lamps 108 of the device 104. For example, the UV curtain may be a tent-like or tunnel-like structure that covers or surrounds the device 104, and possibly the object 102 to be sanitized/disinfected. That way, the light emitted towards the object 102 may be directed only to the object 102 and not elsewhere. Once the device 104 is in a suitable position in order for the lamps 108 to emit light towards the object 102, the UV curtain may be placed over or around the device 104, and once the UV curtain is in a desired position, the lamps 108 may be powered on such that light is directed towards the object 102.

The interior surface of the UV curtain, or the surface of the UV curtain that is facing the device 104/object 102 may include a reflective surface that reflects light back towards the object 102. As a result, instead of the light being potentially directed away from the object 102, the reflective surface may redirect that light back to surfaces of the object 102 to be sanitized/disinfected. The reflective surface may be any type of metal or any type of polyester film having a coating of metal, such as Metallized DuraLar™, which consists of a polyester film with a thin coating of aluminum. Example metals that may be used in association with the reflective surface may include aluminum, mild steel, stainless steel, nickel, silver, chrome plated steel, anodized aluminum, aluminum foil, or any other type of metal.

In various embodiments, a timer and a display may be may be located on the device 104 or may be accessible via a website or mobile application that is associated with the device 104 and that is presented via a user device (e.g., a mobile telephone, a tablet device, a laptop or desktop computer, a display, etc.). Prior to activating the lamps 108, a timer may count down or count up to a predetermined sanitization time. For instance, when the device 104 is powered on, when the device 104 is placed in a suitable location, and/or when object 102 is detected, a time counting down from a predetermined sanitization time may begin. In some instances, upon the predetermined sanitization time being reached (e.g., light has been emitted towards the object 102 for the predetermined sanitization time), an audible cue may be emitted from a speaker and/or another audio device to indicate the predetermined sanitization time has been reached. Alternatively, a visual cue may be displayed via the display that indicates that the predetermined sanitization time has been reached. The predetermined sanitization time may be a time that represents a standardized amount of time that an object 102 should spend under light (e.g., UV light UV-C light) to meet a threshold sanitization level. The threshold sanitization level may be a predetermined sanitization level associated with removing at least a majority of (or a different level, such as 90%, 95%, 99%, etc.) potentially harmful pathogens. In some instances, a timer may be coupled to the device 104 or may be displayed via the mobile application. An operator of the device 104 may utilize the timer to determine a length of time the object 102 is exposed by the light emitted by the lamps 108 of the device 104.

At any location on the device 104, the device 104 may include a control panel that is used to control operations associated with the device 104. The control panel may be affixed to device 104 and include a user interface (or a graphical user interface), one or more buttons, sliders, levers, switches, etc. Using the control panel, an operator of the device 104 may turn on/off the lamps 108 of the device 104, specify a duration in which the lamps 108 are to emit light directed to the object 102, adjust a frequency or wavelength of light emitted by the lamps 108, and so on. That is, using the control panel, a user may cause the lamps 108 to emit light for a particular period of time that will sanitize and disinfect the object 102 to be sanitized/disinfected. In an alternative embodiment, or in addition to use of the control panel, the device 104 may be controlled by other means, such as a remote control or a mobile application residing on a device (e.g., a mobile telephone, a tablet device, a desktop/laptop computer, etc.) that is associated with the device 104 and that is accessible via the device of the operator. Or, the control panel may be separate from the device 104, but be connected to the device 104 via one or more electrical wires or be connected wirelessly (e.g., WiFi, Bluetooth, cellular connection, etc.).

A power source may also be included to provide power (e.g., electricity) to the lamps 108. The power source may be a plug that is inserted into an outlet for electrical power. However, in other embodiments, the apparatus may be operated using other types of power, including a battery, solar power, a gas or diesel engine, propane, etc. In some instances, a single power source may supply electric power to each lamp 108 of the device 104, or different power sources may supply electric power to different lamps 108 of the device 104.

In various embodiments, the device 104 may include an emergency shut-off input mechanism. An emergency shut-off may be a manual button or switch (or a selectable element actuable via the display/mobile application) that turns-off, de-activates, and/or shuts down the lamps 108. For instance, the emergency shut-off may be a lever, switch, button, selectable UI element that, when manually switched or inputted by an operator of the device 104, immediately ceases application of the light by the lamps 108 of the device 104.

Figure 2:
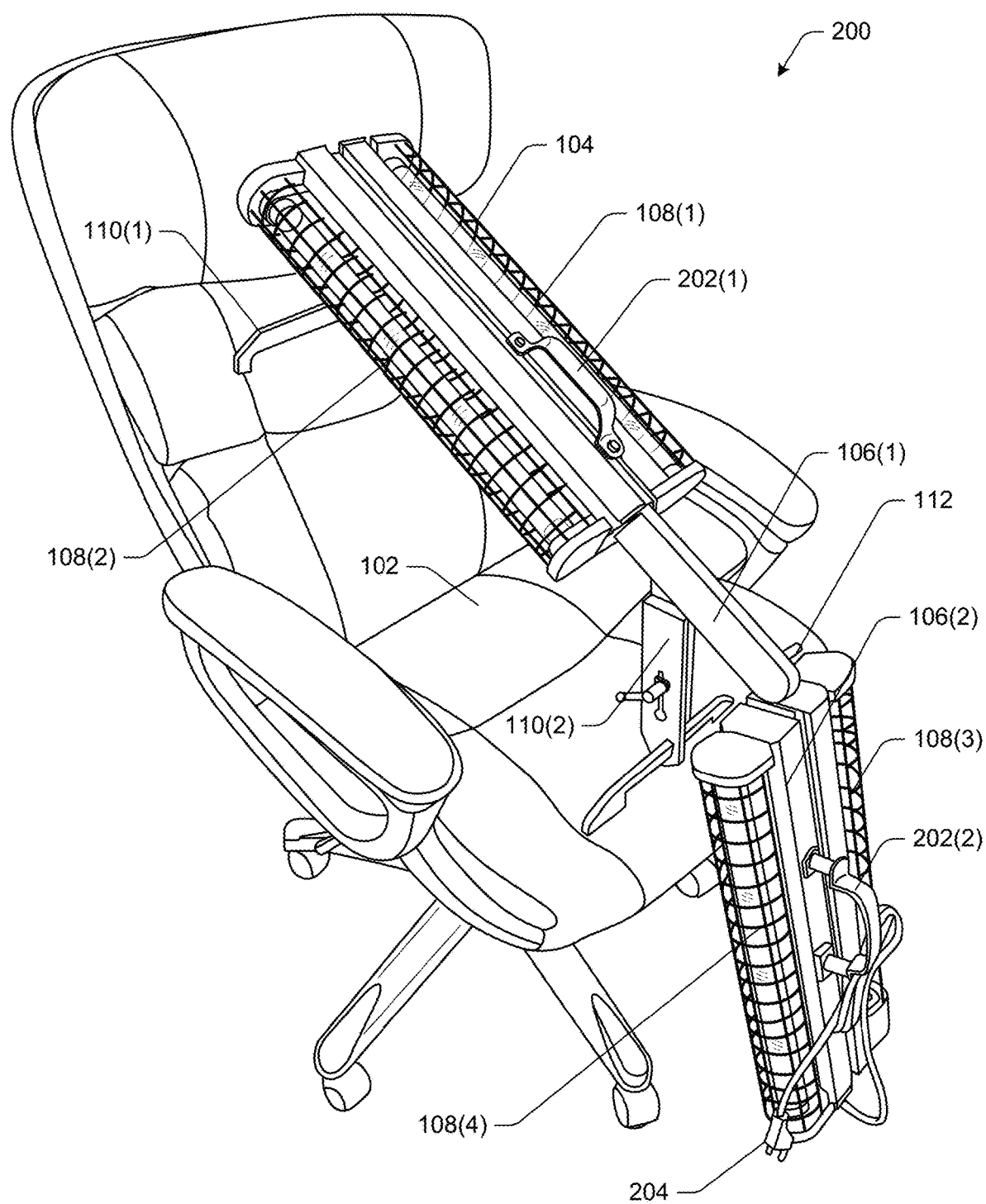
FIG. 2 is a pictorial diagram of an illustrative device as shown in FIG. 1 with respect to a chair.

FIG. 2 is a pictorial diagram 200 of an illustrative device that is configured to sanitize/disinfect an object. The device 104 depicted in FIG. 2 may correspond to the device 104 depicted in FIG. 1, but from a different perspective/angle. Here, the device 104 depicted in FIG. 2 is from a side and top view. As illustrated, although any type of object 102 may be sanitized/disinfected by the device 104, the object 102 is a desk/office chair and the device 104 is positioned over the desk/office chair 102 such that light emitted by the lamp(s) 108 (e.g., UV light, UV-C light, etc.) is directed towards the different surfaces of the chair 102.

As shown, the device 104 includes two rotatable and adjustable arms 106. Although the device 104 may have a single arm 106 or multiple arms 106, the device 104 depicted in FIG. 2 includes a first arm 106(1) that includes any number of lamps 108. In this embodiment, the first arm 106(1) includes two lamps 108—lamp 108(1) and lamp 108(2) that are positioned such that light (also referred to herein as "first light") is emitted towards a top portion of the chair 102. Although any number of lamps 108 may be present, a second arm 106(2) of the device 104 also includes two lamps 108—lamp 108(3) and lamp 108(4) that are positioned such that light (also referred to herein as "second light") is emitted towards a bottom/lower portion of the chair 102. The device 104 may have any number of support arms 110 that support the device 104 and cause the device 104 to be positioned above, below, or to the side of the chair 102. Here, the device 104 includes two support arms 110—a first support arm 110(1) that is coupled to the first arm 106(1) and that is in contact with an upper portion of the chair 102 and a second support arm 110(2) that is also coupled to the first arm 106(1) and that is in contact with a lower portion of the chair 102. However, in other embodiments, the second support arm 110(2) may be coupled to the second arm 106(2). The first arm 106(1) and the second arm 106(2) may be connected and/or coupled to one another via the pivot 112. The pivot 112 may be located on the first arm 106(1), the second arm 106(2), on both the first arm 106(1) and the second arm 106(2), or between the first arm 106(1) and the second arm 106(2). Via the pivot 112, the two arms 106 of the device 104 may each bend or pivot upwards/downwards and may each rotate up to 360 degrees.

The device 104 may include one or more handles 202 that can be used to move the device 104 and to position the device 104 over, under, or to the side of the object 102 to be sanitized/disinfected. Although any number of handles 202 may be included on the device 104, and the handles 202 may be disposed on any location on the device 104, the device 104 includes two handles 202—a first handle 202(1) and a second handle 202(1). The first handle 202(1) may be disposed on the first arm 106(1). Here, the first handle 202(1) is disposed on a top surface of the first arm 106(1) that is opposite of a bottom surface of the first arm 106(1) that is directed towards the chair 102. The second handle 202(1) may be disposed on the second arm 106(2). In this embodiment, the second handle 202(2) is disposed on a top surface of the second arm 106(2) that is opposite of a bottom surface of the second arm 106(2) that is directed towards the chair 102. The first arm 202(1) and/or the second arm 202(2) of the device 104 may be grasped by the hands of an operator of the device 104 in order to move the device 104, position the device 104 at a desired location with respect to the object 102, remove the device 104 away from the object 102 once the object 102 has been sanitized/disinfected, and/or transport or carry the device 104. The handles 102 may be affixed to the device 104 using one or more screws, nails, bolts, adhesive, or any other fastener that allows an operator to move or position the device 104 using the handles 202.

The device 104 also includes a power source 204 that provides electrical power to the lamp(s) 108 of the device 104. The power source 204 may be disposed on any location on the device 104 and may provide electrical power to each of the lamps 108 of the device 104. In this embodiment, the power source may have a cord that is connected to each of the lamps 108. In other embodiments, the device 104 may have multiple power sources 204 that each provide electrical power to one or more of the lamps 108. In certain embodiments, the lamps 108 are powered on and powered off via a power cord having a male end and/or female end. In some instances, the male end of the power cord may protrude via a location on the device 104, where the male end of the power cord is then plugged into an outlet, such as a wall outlet, a power strip, a vehicle outlet, and so on. The power cord enables the device 104 to be powered on/off as a result of the male end of the power cord being connected.

The power source 204 may have an electrical power setting. For instance, the power source 204 may be at least one of 240 volt (240v) single phase, 240v two phase, 240v three phase, 110-volt single phase, or other suitable voltage and phase settings. The power source 204 may be configured to receive electric power from an electrical producing device or system including receive electrical power via chemical energy, mechanical energy, solar energy, wind energy, geothermal energy, hydrogen energy, hydroelectric energy, and/or biomass energy. Although a power cord is described with respect to FIG. 2, it is contemplated that the device 104, and the lamps 208 in particular, may receive electrical power using other types of power, including a port/charger associated with a vehicle, one or more batteries, solar power, a gas or diesel engine, a generator, propane, etc.

The following example illustrates how an object 102, such as a chair, is to be sanitized by the device 104. Initially, device 104 is placed in a position in which the lamps 108 of the device 104 are directed towards the object 102 to be sanitized/disinfected. The handles 202 may be utilized by the operator of the device 104 in order to rotate and/or pivot the arms 106 of the device 104. If a UV curtain is to be used, the UV curtain is placed around the device 104 (and possibly the object 102). In a vehicle setting, the UV curtains may be placed on windows, the windshield, a skylight, and so on. Optionally, the operator may determine a duration of time in which the object 102 is to be sanitized (i.e., a duration of time in which the lamp(s) 108 emit light towards the object 102), such as via a control panel of the device 104 or via a mobile application. However, the device 104 may also be operated using a default or predetermined duration of time. When the object 102 is ready to be sanitized/disinfected, the lamps 108 are enabled to be powered on/off by first plugging the power source 204/cord into an outlet. When in the expanded configuration, the lamps 108 of the device 104 emit light towards the desired surfaces of the object 102 for the preferred duration of time. Once the object 102 has been subject to the light emitted by the lamps 108 for the desired duration of time, in order to power off/disactivate the lamps 108, the male end of the power source 204/cord is disconnected. This will power off the lamps 108 such that no more light will be emitted. Either the sanitized/disinfected object 102 can be removed or the device 104 may be removed using the handles 202. In some embodiments, device 104 itself, or just the arms 106 and/or the lamps 108 of the device 104, may be pivoted or rotated such that the lamps 108 are facing/directed to additional surfaces of the object 102/chair or surfaces of a different object 102. The process described above may then be repeated in order to sanitize/disinfect the additional surfaces of the object 102 or the different object 102.

As stated above with respect to FIG. 2, the lamps 108 may be housed in lamp housings. The lamp housings may provide a coupling mechanism to configure the lamps 108 to be coupled to the arms 106 of the device 104. In addition, the lamp housings may block at least a portion of the light emitted from the lamps 108 (e.g., light emitted in a direction different than that of the object 102). The lamps 108 may be one or more germicidal lamps 108 that disable and/or destroy pathogens (e.g., bacteria, fungi, protozoa, viruses, and/or parasites). The lamps 108 of the device 104 may have different UV lamp settings. As a hypothetical example, a first lamp 108 of the lamps 108 (e.g., lamp 108(1)) may include a first UV setting (e.g., UV-C with a wavelength from 100 nm to 280 nm), a second lamp 108 of the lamps 108 (e.g., lamp 108(2)) may include a second UV setting (e.g., UV-B with a wavelength from 280 nm to 315 nm), a third lamp 108 of the lamps 108 (e.g., lamp 108(3)) may include a third UV setting (e.g., UV-A with wavelength from 315 nm to 400 nm), and so on. In various embodiments, the lamps 108 may emit light that has a wavelength between ten and 400 nanometers. The application of light to an object 102 may disable and/or destroy pathogens (e.g., bacteria). For instance, light may be electromagnetic radiation that is mutagenic (i.e., alters the genetic material or DNA/RNA of bacteria). In some instances, the light may break the molecular bonds of microorganismal DNA/RNA.

Figure 3:
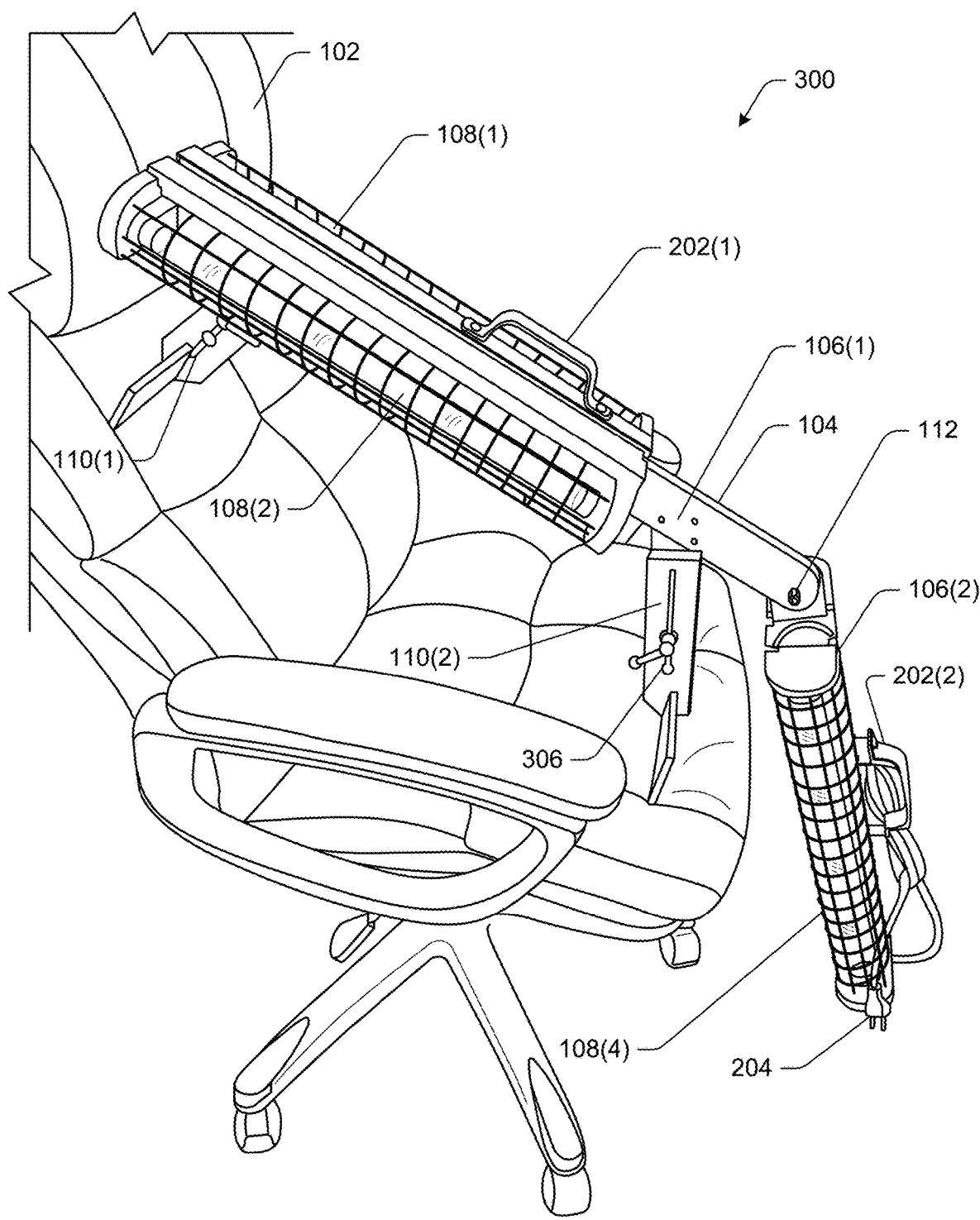
FIG. 3 is a pictorial diagram of an illustrative device as shown in FIG. 2, but from a different perspective as compared to FIG. 2.

FIG. 3 is a pictorial diagram 300 of an illustrative device that is configured to sanitize/disinfect an object. The device 104 depicted in FIG. 3 may correspond to the device 104 depicted in FIG. 2, but from a different perspective/angle. Here, the device 104 depicted in FIG. 3 is from a side view and the object 102 to be sanitized/disinfected is also a chair.

In some embodiments, one or both of the support arms 110 may include an adjuster 306 that allows the support arms 110 to be adjusted upwards and downwards. As shown in FIG. 3, the support arm 110(2) may include an adjuster 306 that allows the support arm 110(2), and the device 104 as a whole, to be adjusted upwards and downwards based on the object 102 to be sanitized/disinfected, the position of the device 104, the orientation of the object 102, the particular surface(s) of the object 102 to be sanitized/disinfected, the size/shape of the object 102, the size of the device 104 relative to the size/shape of the object 102, and so on. Accordingly, the adjuster 306 may allow the device 104 to be adjustable such that the lamps 108 of the device 104 are configured to emit light onto different surfaces of the object 102.

FIG. 4 is a pictorial diagram 400 of an illustrative device that is removably or permanently coupled to an object and that is configured to sanitize/disinfect the object. As described above with respect to FIGS. 1-3, the device 104 is positioned over the object 102 to be sanitized/disinfected using a combination of arms 106, lamps 108, and support arms 110. In FIG. 4, the device 104 is removably affixed or attached to the object 102, although the device 104 may also be permanently attached/affixed to the object 102. Although the device 104 may be affixed/attached to any location on the object 102, FIG. 4 depicts that the device 104 is affixed/attached to different sides of a seat/chair 102. For example, the object 102 may be any number of seats of a vehicle, such as two seats as depicted in FIG. 4.

In 402, FIG. 4 illustrates a general view of the device 104. The device 104 may be permanently or removably attached/affixed to the side of the seats. In other embodiments, the device 104 may be attached to the front, back, top, etc. of the seats. The device 104 may include one or more arms 404 that include a lamp assembly 406 that includes one or more lamps 108. In particular, the device 104 includes a first arm 404(1) that includes a first end that is attached to a first side of the seats and a second arm 404 that includes a first end that is attached to a second, opposite side of the seats. Second ends of each of the first arm 404(1) and the second arm 404(2) are coupled to different sides/ends of the lamp assembly 406 such that the lamp assembly 406, and the lamp(s) 108 included therein, are positioned over and above the seats to be sanitized/disinfected. In other words, the first arm 404(1) is attached to a first side of the lamp assembly 406 and the second arm 404(1) is attached to a second, opposite side of the lamp assembly 406. That way, the lamps 108 may emit light towards the surface of the object 102, such as the seats illustrated in FIG. 4. As described herein, the arms 404 and the lamp assembly 406 may rotate such that the lamps 108 are able to emit light towards different surfaces or portions of the seats. The arms 406 may be permanently or removably coupled/affixed to the side of the seats in any manner, including pins, snaps, etc. Although two arms 404 are shown in FIG. 4, a single arm 404 may include or support the lamp 108/lamp assembly 406.

In 408, the device 104 is shown from a side perspective/angle from the side of the seats. In 410, the device 104 is shown from a top perspective/angle from over the seats. In 412, the device 104 is shown from front perspective/angle from in front of the seats. In each of 408, 410, and 412, the device 104 includes two arms (404(1) and 404(2)) that are removably or permanently attached to the object 102 (e.g., the sides of the seats) and that include the lamp assembly 406 that includes the lamps 108 that emit light directed towards the front surfaces of the seats.

The device 104 depicted in FIG. 4 can be considered an upper mounted unit, as illustrated in 414. For instance, the device 104 may begin in an upright configuration or orientation proximate to an upper portion or top of the seats and then rotate downwards towards a lower portion or bottom of the seats. The upright configuration may correspond to a beginning position of the device 104 prior to the device 104 sanitizing/disinfecting the object 102. The lamps 108 of the lamp assembly 406 may emit light constantly as the lamp assembly 406/lamps 108 rotate downwards. However, in other embodiments, the lamps 108 may emit light towards the seats but the arms 404/lamp assembly may stop moving/rotating at different positions or locations for a duration of time. As a result, the lamps 108 may emit light and sanitize different surfaces of the seats at different intervals or different times as the arms 404/lamp assembly rotate downwards. Although the arms 404/lamp assembly 406 may stop moving any number of times in order to emit light at different positions, FIG. 4 illustrates that the arms 404/lamp assembly 406 may cease moving at five different locations. The arms 404/lamp assembly 406 may begin at position 416 and then rotate to position 418 where the lamps 108 emit light towards the seats for a duration of time. After that duration of time, the arms 404/lamp assembly rotates to positions 420 and 422, where the lights 108 also emit light towards the seats for durations of time, which may be the same or different from the duration of time at position 418. The arms 404/lamp assembly then rotates to its final position at 424, where the lamps 108 may or may not emit light at this final position. Once the emitted light has sanitized/disinfected the various surfaces of the seats, the arms 404/lamp assembly may be returned/rotated upwards to its initial position/configuration at 416.

In some embodiments, the arms 404/lamp assembly 406 may be moved between different positions manually by an operator of the device 104, such as being rotated physically or by using a remote control or via a user interface presented via a user device. Alternatively, or in addition, the device 104 may rotate in a fully automated or partially automated manner. The light emitted by the lamps 108 may continuously emit light while the device 104 is rotating, or the light may only be emitted by the lamps 108 while the arms 404/lamp assembly 406 are at a non-moving position for a specified duration of time. As a result of the arms 404/lamp assembly 406 of the device 104 rotating about the object 102/seats, various surfaces of the object 102/seats may be exposed to the light emitted by the lamps 108 and, therefore, sanitized/disinfected (with pathogens removed or diminished).

FIG. 5 is a pictorial diagram 500 of an illustrative device that is removably or permanently coupled to an object and that is configured to sanitize/disinfect the object. As described above with respect to FIGS. 1-3, the device 104 is positioned over the object 102 to be sanitized/disinfected using a combination of arms 106, lamps 108, and support arms 110. In FIG. 5, like FIG. 4, the device 104 is removably affixed or attached to the object 102, although the device 104 may also be permanently attached/affixed to the object 102. Although the device 104 may be affixed/attached to any location on the object 102, FIG. 5 depicts that the device 104 is affixed/attached to the side of a seat/chair 102. For example, the object 102 may be any number of seats of a vehicle, such as two seats as depicted in FIG. 5.

In 502, FIG. 5 illustrates a general view of the device 104. The device 104 may be permanently or removably attached/affixed to the side of the seats. In other embodiments, the device 104 may be attached to the front, back, top, etc. of the seats. The device 104 may include one or more arms 404 that include a lamp assembly 406 that includes one or more lamps 108. In particular, the device 104 includes a first arm 404(1) that has a first end that is attached to a first side of the seats and a second arm 404 that has a first end that is attached to a second, opposite side of the seats. Second ends of each of the first arm 404(1) and the second arm 404(2) are coupled to different sides of the lamp assembly 406 such that the lamp assembly 406, and the lamp(s) 108 included therein, are positioned over and above the seats to be sanitized/disinfected. In other words, the second end of the first arm 404(1) is attached to a first side of the lamp assembly 406 and the second end of the second arm 404(1) is attached to a second, opposite side of the lamp assembly 406. That way, the lamps 108 may emit light towards the surface of the object 102, such as the seats illustrated in FIG. 5. As described herein, the arms 404 and the lamp assembly 406 may rotate such that the lamps 108 are able to emit light towards different surfaces of the seats. The arms 406 may be permanently or removably coupled/affixed to the side of the seats in any manner, including pins, snaps, etc. Although two arms 404 are shown in FIG. 5, a single arm 404 may include or support the lamp 108/lamp assembly 406.

In 504, the device 104 is shown from a side perspective/angle from the side of the seats. In 506, the device 104 is shown from a top perspective/angle from over the seats. In 508, the device 104 is shown from front perspective/angle from in front of the seats. In each of 504, 506, and 508, the device 104 includes two arms (404(1) and 404(2)) that are removably or permanently attached to the object 102 (e.g., the sides of the seats) and that include the lamp assembly 406 that includes the lamps 108 that emit light directed towards the front surfaces of the seats.

The device 104 depicted in FIG. 5 can be considered lower mounted unit, as illustrated in 510. For instance, the device 104 may begin in a lower or nearly horizontal configuration or orientation proximate to a lower portion or a bottom of the seats (e.g., a starting position) and then rotate upwards towards an upper portion or top of the seats. The lamps 108 of the lamp assembly 406 may emit light constantly as the lamp assembly 406/lamps 108 rotate upwards. However, in other embodiments, the lamps 108 may emit light towards the seats but the arms 404/lamp assembly may stop moving/rotating at different positions or locations for a duration of time. As a result, the lamps 108 may emit light and sanitize different surfaces of the seats at different intervals or different times as the arms 404/lamp assembly rotate upwards. Although the arms 404/lamp assembly 406 may stop moving any number of times in order to emit light at different positions, FIG. 5 illustrates that the arms 404/lamp assembly 406 may cease moving at four different locations. The arms 404/lamp assembly 406 may begin at position 512 and then rotate to position 514 where the lamps 108 emit light towards the seats for a duration of time. After that duration of time, the arms 404/lamp assembly rotates to position 516, where the lamps 108 emit light towards the seats for a duration of time. The arms 404/lamp assembly then rotates to its final position at 518, where the lamps 108 may or may not emit light at this final position. Once the emitted light has sanitized/disinfected the various surfaces of the seats, the arms 404/lamp assembly may be returned/rotated downwards to its initial position/configuration at 512.

In some embodiments, the arms 404/lamp assembly 406 may be moved between different positions manually by an operator of the device 104, such as being rotated physically or by using a remote control or via a user interface presented via a user device. Alternatively, or in addition, the device 104 may rotate in a fully automated or partially automated manner. The light emitted by the lamps 108 may continuously emit light while the device 104 is rotating, or the light may only be emitted by the lamps 108 while the arms 404/lamp assembly 406 are at a non-moving position for a specified duration of time. As a result of the arms 404/lamp assembly 406 of the device 104 rotating about the object 102/seats, various surfaces of the object 102/seats may be exposed to the light emitted by the lamps 108 and, therefore, sanitized/disinfected (with pathogens removed or diminished).

Figure 6:
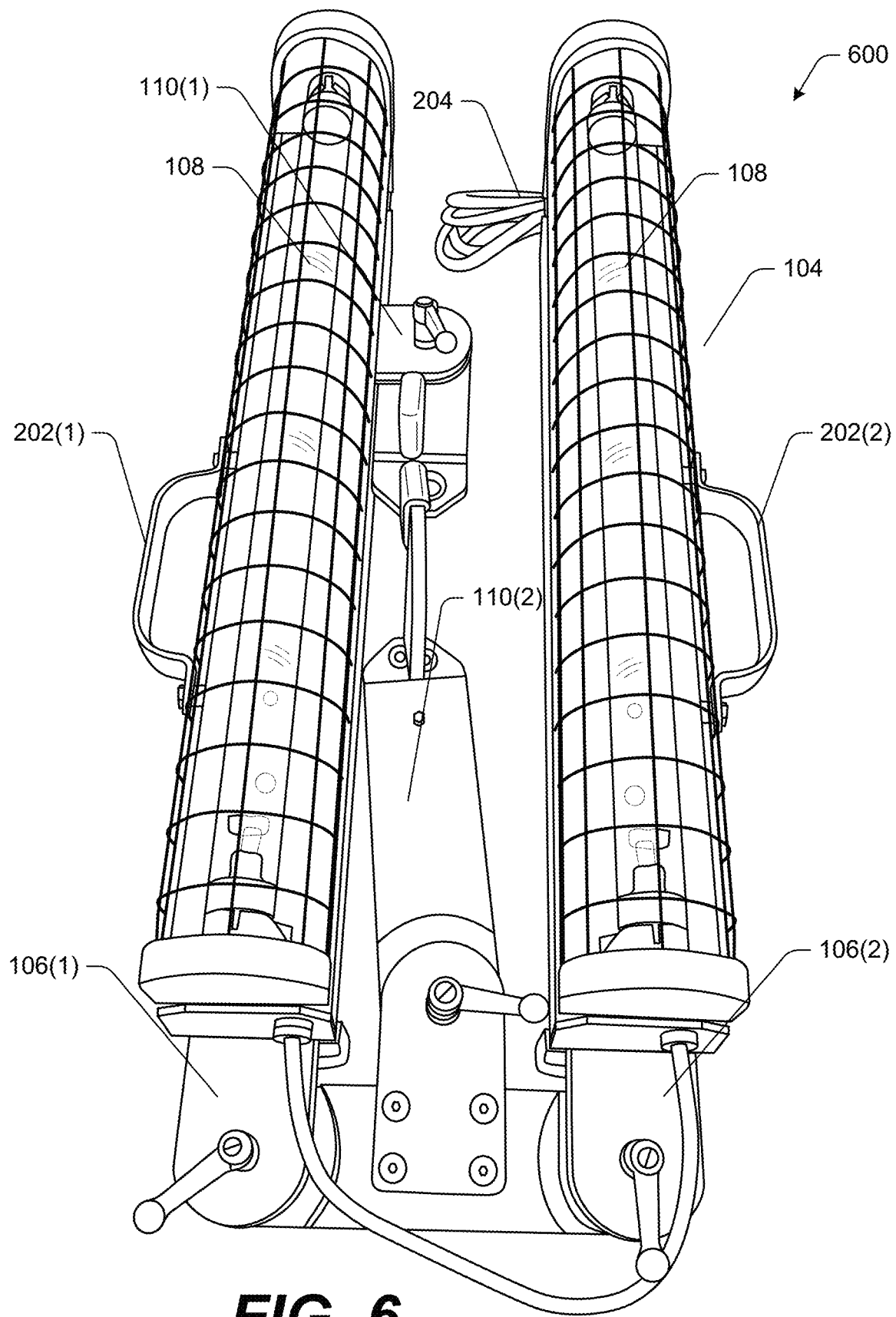
FIG. 6 is a pictorial diagram of an illustrative device in a condensed, unexpanded, or folded configuration.

FIG. 6 is a pictorial diagram 600 of an illustrative device that is in a collapsed or configuration. The device 104 depicted in FIG. 6 may correspond to the device 104 illustrated in FIGS. 1-3. However, the device 104 depicted in FIGS. 1-3 is in the expanded configuration such that the lamps 108 of the device 104 are able to emit light towards an object 102 in order to sanitize/disinfect the object 102. Here, in FIG. 6, the device 104 is in the collapsed configuration when the device 104 is not in use or is being transported. The device 104 may transition between the expanded configuration and the collapsed configuration by rotating around the pivot 112. The device 104 may also have multiple pivots 112 that allow each arm 106 of the device to bend/rotate and collapse inwards to result in the collapsed configuration of the device 104. For instance, the device 104 may be associated with (or be in contact with) a first pivot that enables the first arm 106 to rotate inwards towards a second arm 106, and the second arm 106 may be associated with (or be in contact with) a second pivot that enables the second arm 106 to rotate inwards towards the first arm 106. FIG. 6 also illustrates the lamps 108 within each of the lamp assemblies included on the arms 106(1) and 106(2).

In some embodiments, some type of fastener may be utilized to maintain the device 104 in the collapsed configuration and so that the device 104 does not unexpectedly transition to the expanded configuration. The fasteners may be any type of mechanism that causes the device 104 to remain in the collapsed configuration, particularly when the device 104 is not in use or is being transported. The fasteners may include straps, buckles, zippers, Velcro®, buttons, clips, ties (e.g., string or rope), or any other mechanism that will keep the device in the collapsed configuration. While in the collapsed configuration, one or both of the handles 202(1) and 202(1) may be used to hold, lift, carry, or otherwise transport the device 104 when the device 104 is not in use. As shown, although the device 104 may have any number of handles 202, FIG. 6 illustrates that the device has two handles 202 disposed on opposite sides of the device 104 (e.g., a first handle 202(1) on first arm 106(1) and a second handle 202(2) on second arm 106(2). As a result, when not in use, the device 104 may be lifted, held, carried, etc. using one or two hands, or by hands of different individuals.

Figure 7:
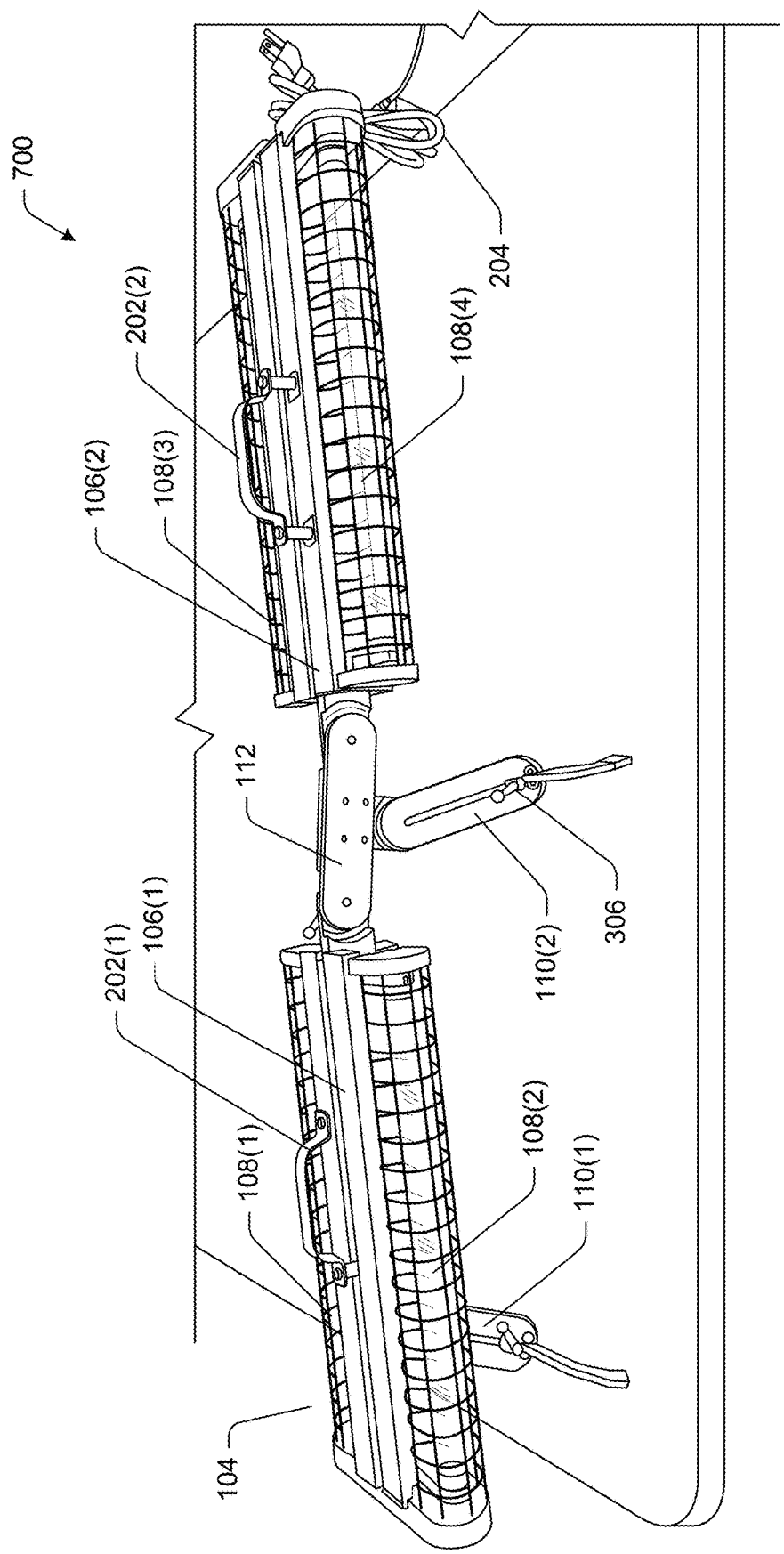
FIG. 7 is a pictorial diagram of an illustrative device as shown in FIG. 2, but from a different perspective as compared to FIGS. 1-3 and 6.

FIG. 7 is a pictorial diagram 700 of an illustrative device that is used to sanitize/disinfect an object. The device 104 shown in FIG. 7 may correspond to the device 104 illustrated in FIGS. 1-3 and 6, but is shown from a different perspective/angle. Here, in 700, the device 104 is shown from a side perspective/angle and is located on some type of hard surface, such as the ground or a table. FIG. 7 illustrates the multiple lamps 108, with one lamp 108 and corresponding lamp assembly on each side of each arm 106. The other features/components of the device 104 illustrated in FIG. 7 are the same as, or are similar to, the features/components of the device 104 depicted in FIGS. 1-3 and 6.

Figure 8:
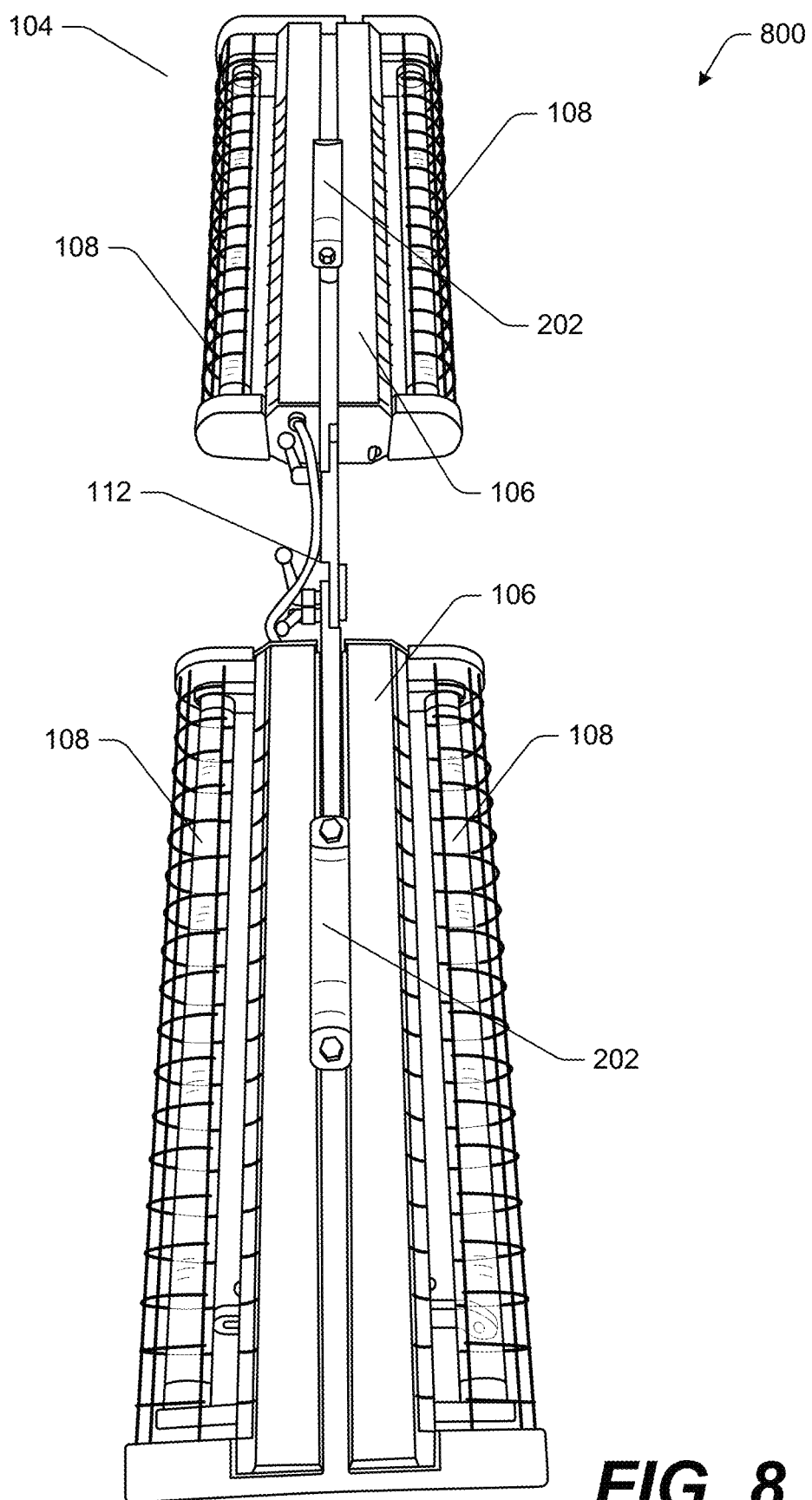
FIG. 8 is a pictorial diagram of an illustrative device as shown in FIG. 2, but from a different perspective as compared to FIGS. 1-3, 6, and 7.

FIG. 8 is a pictorial diagram 800 of an illustrative device that is used to sanitize/disinfect an object. The device 104 shown in FIG. 8 may correspond to the device 104 illustrated in FIGS. 1-3, 6, and 7, but is shown from a different perspective/angle. Here, in 800, the device 104 is shown from a top perspective/angle that is from over the device 104. FIG. 8 illustrates the multiple lamps 108, with one lamp 108 and corresponding lamp assembly on each side of each arm 106. The other features/components of the device 104 illustrated in FIG. 8 are the same as, or are similar to, the features/components of the device 104 depicted in FIGS. 1-3, 6, and 7.

Figure 9:
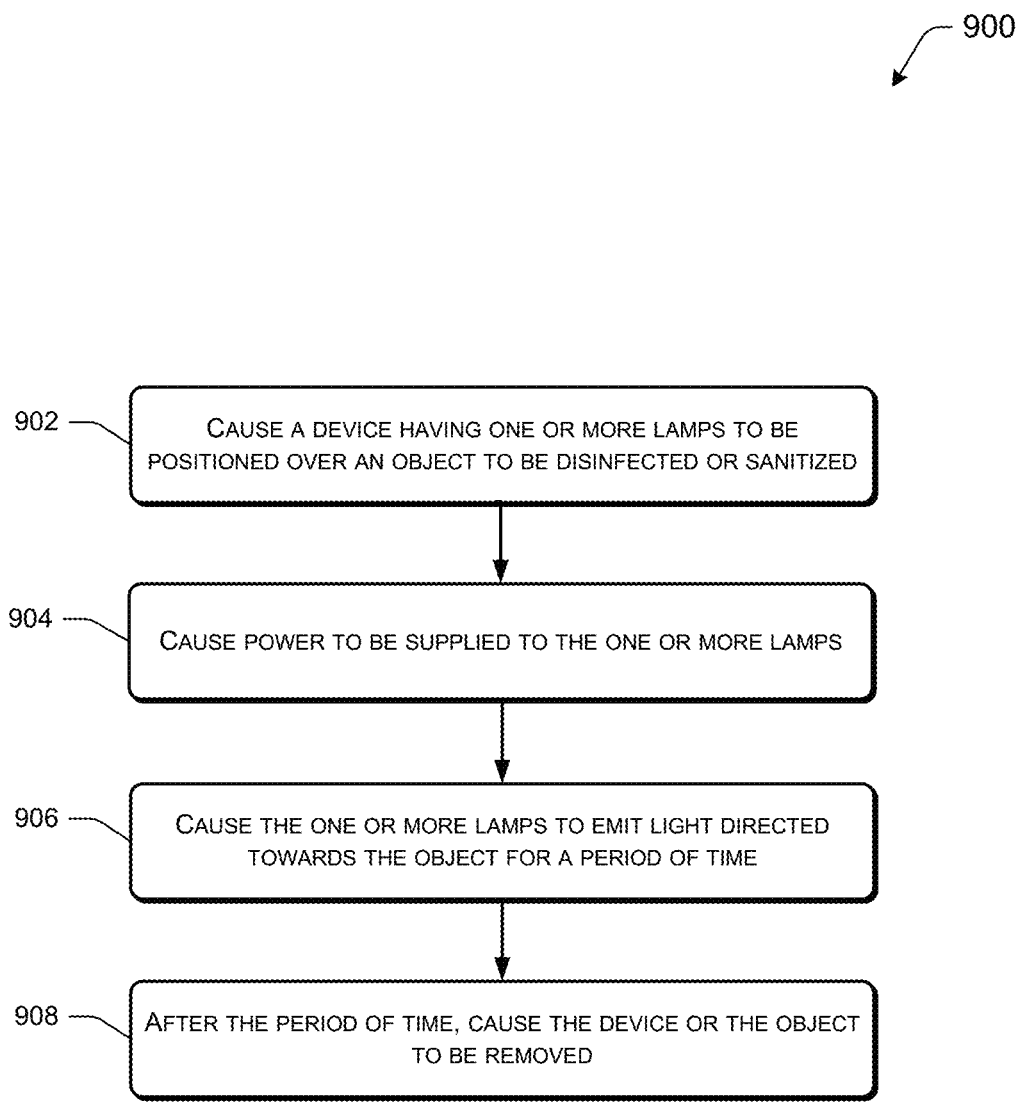
FIG. 9 is a flow diagram directed to causing a device to disinfect or sanitize one or more surfaces of an object using light emitted by one or more lamps of the device.

FIG. 9 is a flow diagram 900 illustrating an example process for sanitizing/disinfection an object using a device having lamps that emit light, such as UV light or UV-C light. The operations illustrated in FIG. 9 may be performed by the device 104 illustrated in FIGS. 1-8, or another similar device.

Block 902 states causing a device having one or more lamps to be positioned over an object to be disinfected. As described herein, the one or more lamps 108 of the device 104 may emit light to sanitized/disinfected and the one or more handles 202 of the device 104 may be used to place the device 104 over, underneath, to the side of, etc. the object 102 to be sanitized/disinfected (e.g., vehicle seats). The device 104 may be positioned over the object 102 using one or more support arms 110 that are coupled or attached to one or more arms 106 of the device 104.

Block 904 states causing power to be supplied to the one or more lamps. Once the device 104 is placed in a position to sanitize/disinfect the object 102, the lamp(s) 108 of the device 108 may be powered using the power source 204, such as by a plug of the device 104 being plugged into an outlet or an adapter within the vehicle. Upon the power source being plugged in, the lamp(s) 108 may receive electrical power and may emit light (e.g., UV light, UV-C light, etc.) directed towards the object 102.

Block 906 states causing the one or more lamps to emit light directed towards the object for a period of time. As stated above, the lamp(s) 108 may direct light towards the object 102 for a duration of time that is sufficient to destroy, eliminate, or significantly reduce the number of pathogens (e.g., bacteria, viruses, mold, etc.) that reside on one or more surfaces of the object 102.

Block 908 illustrates after the period of time, causing the device or the object to be removed. Once the duration of time has concluded, the device 104 may be removed using the handle(s) 202 or another part of the device 104. Alternatively, the object 102 may be removed from being underneath the device 104.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A device configured to sanitize one or more seats of a vehicle, comprising:
    a first arm;
    a second arm physically connected to the first arm via one or more pivot points;
    one or more first lamps that are disposed on the first arm and that emit first light directed towards the one or more seats;
    one or more second lamps that are disposed on the second arm and that emit second light towards the one or more seats, wherein the first light and the second light are ultraviolet (UV) light or ultraviolet-C (UV-C) light;
    a first support arm that is directly coupled to the first arm and that is in contact with the one or more seats while the first light and the second light are being emitted; and
    a second support arm that is directly coupled to the first arm, the second arm, or a component connecting the first arm and the second arm, and that is in contact with the one or more seats while the first light and the second light are being emitted.

2. The device as recited in claim 1, wherein at least the first support arm or the second support arm is adjustable to vary a distance between the one or more seats and the device.

3. The device as recited in claim 1, further comprising a power source configured to supply electric power to the one or more first lamps and the one or more second lamps.

4. The device as recited in claim 3, wherein:
    the power source is a power cord having a male end; and
    the one or more first lamps are configured to emit the first light and the one or more second lamps are configured to emit the second light at a time at which the male end is plugged into an electrical outlet.

5. The device as recited in claim 1, wherein the device is configured to transition between an expanded configuration while the first light and the second light are being emitted and a collapsed configuration based at least in part on the first arm or the second arm rotating or pivoting about the one or more pivot points.

6. The device as recited in claim 1, further comprising:
    one or more first lamp housings that are disposed on the first arm and that include the one or more first lamps; and
    one or more second lamp housings that are disposed on the second arm and that include the one or more second lamps.

7. The device as recited in claim 1, wherein the one or more pivot points enable the first arm or the second arm to rotate or pivot with respect to the one or more seats based at least in part on an orientation or a position of the one or more seats.

8. The device as recited in claim 1, further comprising:
    a first handle disposed on a first side of the first arm that is opposite the one or more seats; and
    a second handle disposed on a second side of the second arm that is opposite the one or more seats.

9. A device comprising:
    a first arm;
    a second arm that is associated with the first arm via one or more pivot points;
    one or more first lamps that are disposed on the first arm and that emit first light directed towards an object;
    one or more second lamps that are disposed on the second arm and that emit second light towards the object;
    a first support arm that is directly coupled to the first arm and that is in contact with the object to maintain a distance between the device and the object; and
    a second support arm that is directly coupled to the first arm, the second arm, or a component connecting the first arm and the second arm, and that in contact with the object to maintain the distance between the device and the object.

10. The device as recited in claim 9, wherein the object is one or more seats of a vehicle.

11. The device as recited in claim 9, wherein the first light and the second light are ultraviolet (UV) light or UV-C light.

12. The device as recited in claim 9, wherein:
    the first support arm is in contact with the object while the first light and the second light are being emitted; and
    the second support arm is in contact with the object while the first light and the second light are being emitted, wherein at least the first support arm or the second support arm is adjustable to adjust the distance.

13. The device as recited in claim 9, further comprising a power source configured to supply electric power to the one or more first lamps and the one or more second lamps, wherein:
    the power source is a power cord having a male end; and
    the one or more first lamps are configured to emit the first light and the one or more second lamps are configured to emit the second light at a time at which the male end is plugged into an electrical outlet.

14. The device as recited in claim 9, wherein the device is configured to transition between an expanded configuration while the first light and the second light are being emitted and a collapsed configuration based at least in part on the first arm or the second arm rotating or pivoting about the one or more pivot points.

15. The device as recited in claim 9, further comprising:
    a first handle disposed on a first side of the first arm that is opposite the object; and
    a second handle disposed on a second side of the second arm that is opposite the object.

16. A method comprising:
    causing a device to be disposed over an object, the device including:
        a first arm;
        a second arm that is associated with the first arm via one or more pivot points;
        a first support arm that is directly coupled to the first arm and that is in contact with the object to maintain a distance between the device and the object; and
        a second support arm that is directly coupled to the first arm, the second arm, or a component connecting the first arm and the second arm, and that is in contact with the object to maintain the distance between the device and the object; and
    causing activation of the device such that one or more first lamps that are disposed on the first arm emit first light directed towards an object and one or more second lamps that are disposed on the second arm emit second light towards the object, the first light and the second light being emitted for a duration of time.

17. The method as recited in claim 16, wherein the object is one or more seats of a vehicle.

18. The method as recited in claim 16, wherein the first light and the second light are ultraviolet (UV) light or UV-C light.

19. The method as recited in claim 16, wherein:
the first support arm is in contact with the object while the first light and the second light are being emitted; and
the second support arm is in contact with the object while the first light and the second light are being emitted,
wherein at least the first support arm or the second support arm is adjustable to adjust the distance.

20. The method as recited in claim 16, wherein the device further includes a first handle disposed on a first side of the first arm that is opposite the object and a second handle disposed on a second side of the second arm that is opposite the object.

* * * * *